United States Patent
Dingerdissen et al.

(10) Patent No.: US 6,303,800 B1
(45) Date of Patent: Oct. 16, 2001

(54) METHOD FOR PRODUCING PROPENE OXIDE

(75) Inventors: Uwe Dingerdissen, Seeheim-Jugenheim; Holger Orzesek, Gelsenkirchen-Buer; Wilhelm Maier, Essen; Rolf Schulz, Dinslaken, all of (DE)

(73) Assignee: Aventis Research & Technologies GmbH & Co KG (DE)

( * ) Notice: Subject to any disclaimer, the term of this patent is extended or adjusted under 35 U.S.C. 154(b) by 0 days.

(21) Appl. No.: 09/555,978

(22) PCT Filed: Dec. 3, 1998

(86) PCT No.: PCT/EP98/07862

§ 371 Date: Jul. 14, 2000

§ 102(e) Date: Jul. 14, 2000

(87) PCT Pub. No.: WO99/29679

PCT Pub. Date: Jun. 17, 1999

(30) Foreign Application Priority Data

Dec. 8, 1997 (DE) ................................ 197 54 303

(51) Int. Cl.$^7$ .................................................. C07D 301/10
(52) U.S. Cl. ........................... 549/523; 549/532; 549/533
(58) Field of Search .................................... 549/523, 532, 549/533

(56) References Cited

U.S. PATENT DOCUMENTS

| 2,530,509 | 11/1950 | Cook | 260/348.5 |
| 3,026,333 | 3/1962 | Wegner et al. | 260/348.5 |
| 5,241,088 | 8/1993 | Meyer et al. | 549/523 |

FOREIGN PATENT DOCUMENTS

| 2115752 | 7/1972 | (FR) . |
| 93/03065 | 2/1993 | (WO) . |

OTHER PUBLICATIONS

Derwent Abstract of Class E13, Accession No. 76–26524X, XP–002095385 & Canadian 986,127 (Union Carbide Corp.), (Mar. 1976).

*Primary Examiner*—Ba K. Trinh
(74) *Attorney, Agent, or Firm*—Connolly Bove Lodge & Hutz LLP

(57) ABSTRACT

Process for preparing propene oxide, in which a mixture of propene and oxygen or an oxygen-containing gas is reacted at a temperature in the range from 150 to 500° C., in the presence or absence of a catalyst, in a reactor, wherein all or part of the interior of the reactor is lined with inert materials. The inert material used is at least one of the materials of the following group: one or more noble metals of transition group VIII of the Periodic Table, in particular gold, titanium and tantalum, glass, enamel, quartz, ceramic and Teflon. The selectivity to propene oxide is >60%.

5 Claims, No Drawings

METHOD FOR PRODUCING PROPENE OXIDE

This application is a 371 of PCT/EP98/07862 dated Dec. 3, 1998.

The present invention relates to a process for preparing propene oxide by direct oxidation of propene using oxygen or oxygen-containing gases in the gas phase with or without participation of an additionally added catalyst in a temperature range from 150 to 500° C. in a reactor which is lined or modified with inert materials.

Propene oxide is one of the most important intermediates of the chemical industry; it is required mainly for the preparation of propylene glycols which are mostly processed further to give polyurethanes. Bifunctional polypropylene glycols having high viscosities or mixed adducts of propene oxide and ethylene oxide or the monoalkyl ethers of these compounds are important raw materials which are used for producing a wide variety of products (e.g. antifoams, mold release agents, demulsifiers, brake fluids, metalworking auxiliaries, textile assistants, lubricants and adhesives).

Propene oxide itself is a good solvent for cellulose acetate, nitrocellulose, adhesives, resins and other materials and is used as stabilizer for chlorine-containing polymers, as corrosion inhibitor in cooling fluids and pest control compositions and also as a weed killer and as a disinfection and sterilization agent.

There has hitherto been no satisfactory direct oxidation process for preparing propene oxide, since relatively large amounts of by-products or waste products are always produced in addition to propene oxide itself and these have to be separated off in further work-up steps. Furthermore, in the coupled product processes, a use also has to be available for the coproduct or an appropriate price has to be achieved in order to cover costs.

In the conventional chlorohydrin process, the chlorohydrin prepared from propene and chlorine in aqueous solution is dehydrochlorinated using milk of lime ($Ca(OH)_2$). This results in formation of a $CaCl_2$ solution which, after work-up, is disposed of into the wastewater and represents considerable environmental pollution. In the brine recirculation method, the chlorohydrin is reacted with NaOH from the cell liquid of a chloralkali electrolysis, giving an NaOH/NaCl solution which has to be concentrated and freed of organic substances before it can be returned to the electrolysis cell.

The preparation of propene oxide by indirect oxidation using peroxides or peracids is likewise a two-stage process which differs from the chlorohydrin process in that the coproducts formed are frequently obtained in larger amounts than propene oxide itself and an outlet has to be available for them too. Hydrogen peroxide, organic peracids and organic hydroperoxides are used for the epoxidation of propene. The epoxidation using $H_2O_2$ is usually carried out in the liquid phase (e.g. methanol/water) in the presence of a catalyst ($MoO_3$) or titanium oxide on $SiO_2$ or Ti-containing zeolites such as TS-1 (Enichem) at 40–50° C. and a pressure of 4 bar. Propene oxide selectivities of 75–99%, albeit at very low conversions, are reported. Main disadvantages are the high cost of $H_2O_2$ and the difficulty of handling it.

In the oxidation by means of organic peracids, use is made of perpropionic acid and peracetic acid (Daicel), and propene oxide and the corresponding carboxylic acid are formed in the liquid phase. In this context, mention should be made of the Bayer-Degussa process in which acetic acid or propionic acid is reacted with the expensive $H_2O_2$ to generate the peracids which react with propene to give propene oxide and the corresponding acid. The main disadvantage of this coupled product process is once again the formation of large amounts of the corresponding by-products, i.e. the acids, for which there has to be a market and which lower the flexibility of the process. Oxidation using organic hydroperoxides has gained importance in recent years, since there is increasing demand on the world market for the coproducts formed, especially styrene or methyl tert-butyl ether (MTBE). Hydroperoxides used are preferably tert-butyl hydroperoxide, ethylbenzene hydroperoxide and cumene hydroperoxide, which give isobutene (or methyl tert-butyl ether), styrene and methylstyrene, respectively, as coproducts. The SMPO process of Shell, which produces propene oxide together with styrene in a coupled process, uses a $TiO_2$-containing silica gel catalyst (e.g. EP-A-0 345 856). This process is at present profiting from good world market prices for styrene.

Oxidations in the liquid phase, which can be carried out with or without catalyst (homogeneous or heterogeneous) (FR-A-2 115 752, DE-A-4 447 231), do often give better yields than the gas-phase processes, but they are associated with difficult separation tasks, corrosion problems and complicated technologies, so that no industrial-scale use has become known to the present time.

A Canadian publication (CA 986127) describes a gas-phase reaction of propene (93.9%) with oxygen (6.1%) in a glass-lined steel autoclave at a temperature of 226° C. at 5 bar pressure. After 90 minutes, the selectivity to propene oxide is 64% (no indication of the conversion is given). This process has, in particular, the disadvantages of the excessively long residence time and the use of relatively expensive pure oxygen which represents a very high safety risk.

Numerous patents of Odin Corporation (U.S. Pat. Nos. 5,117,011; 5,142,070; 5,241,088; EP-A-0 268 870) disclose processes and reactors for the oxidation of propene in the gas phase under superatmospheric pressure, some of which make use of an alkali metal nitrate melt as catalyst while others proceed in the absence of a catalyst. The best selectivity to propene oxide reported here is 60.8% at a propene conversion of 8.3% (U.S. Pat. No. 5,142,070).

All catalytic and noncatalytic direct oxidation processes for converting propene into propene oxide in the gas phase known in the past have the disadvantage that both the conversions and the selectivities to PO are not very high. For this reason, none of these processes is used industrially at present.

It is therefore an object of the present invention to provide a process for preparing propene oxide by direct oxidation of propene, which process does not have the disadvantages of the known process, i.e. enables propene oxide selectivities of >60% to be achieved without by-products or coproducts in stoichiometric amounts being formed.

It has now surprisingly been found that propene oxide can be prepared very selectively, effectively and inexpensively in a continuous gas-phase process in a reactor lined with inert materials. According to the invention, the inner walls of the reactor and/or internals for directing the gas stream or internals which control the flow of reactants in the tube reactor, e.g. thermocouples, can be coated with an inert material or consist of such a material.

The present invention accordingly provides a process for preparing propene oxide, in which a mixture of propene and oxygen or an oxygen-containing gas is reacted at a temperature in the range from 150 to 500° C., in the presence or absence of a catalyst, in a reactor, wherein all or part of the interior of the reactor is lined with inert materials.

It has surprisingly been found that a tube reactor coated on the inside with inert materials gives better propene oxide yields even without catalyst than does a reactor of the same diameter made of normal standard steel (e.g. V2A). The product selectivity can even be increased here via the moisture and $CO_2$ content of the air or gas mixture used for oxidation.

For the purposes of the invention, inert materials are materials which undergo only minimal, if any, interactions or chemical reactions with the reactants and allow no chemisorption or physisorption on their surface. Inert materials which are suitable for coating the reactor interior or for coating reactor internals can, for example, be selected from the materials of the following group: one or more noble metals of transition group VIII of the Periodic Table, in particular gold, titanium and tantalum, glass, enamel, quartz, ceramic and Teflon.

The process of the invention is preferably carried out continuously using air as oxidant for the propene. This makes a complex work-up superfluous. Unreacted propene is, preferably after separating off the propene oxide, the inert gases and the by-products, recirculated to the feed stream to the reactor.

The reaction temperature is in the range from 150 to 500° C., preferably in the range from 220 to 380° C., at a pressure in the reactor in the range from 1 to 100 bar, in particular from 10 to 55 bar.

According to the invention, the residence times of the gas mixture in the reactor are from 0.1 to 15 minutes, preferably from one to 1000 seconds, particularly preferably from 2.5 to 500 seconds. Furthermore, the process described differs from the previously known gas-phase oxidation processes in that the reaction is carried out continuously in a pressure-rated reactor at hydrodynamic residence times in the region of seconds, in contrast to many previously described autoclave processes with residence times in the region of minutes to hours.

In the process of the invention, the feed gas stream preferably has the following composition: from 50 to 95% by volume of propene and from 5 to 50% by volume of an oxygen-containing gas, e.g. air, or a mixture of oxygen and inert gases (ratio: from 0.1 to 10).

Suitable inert gases are, for example, propane, carbon dioxide, steam, methane, nitrogen or argon.

A further advantage of the process of the invention is that it may be possible to dispense with the addition of any catalyst material, so that separation, work-up, disposal or regeneration of the catalyst material at a later point in time is no longer necessary, which leads to considerable cost and time advantages (reactor dead times are largely dispensed with) in a continuous process.

However, it is also possible to carry out the process of the invention in the presence of heterogeneous catalysts. As catalysts, particular preference is given to compounds based on the transition metals, very particularly preferably those based on titanium, vanadium, chromium, iron, cobalt, nickel, copper, molybdenum, ruthenium, palladium, tungsten, rhenium and silver.

Optimized design of the flow tube and the internals of the reactor allow conversion and selectivity of the process to be optimized even further. The use of shell-and-tube reactors allows the process to be scaled up at will to industrially interesting volume flows. The use of air of suitable purity or with addition of agents for suppressing particular secondary reactions makes it possible to achieve a further increase in the selectivity to propene oxide. Such reagents or inhibitors will be well known to those skilled in the art; preference is often given to using chlorine-containing organic compounds, particularly alkyl chlorides, in particular 1,2-dichloroethane, for this purpose.

The achieved selectivities to propene oxide (based on propene, which is used in excess) are over 60%; the most important by-products are acrolein and acetaldehyde. At this point, it should be remarked that a reaction route known from the literature is the oxidation of acetaldehyde to peracetic acid which then transfers oxygen to propene to form propene oxide and acetic acid as coproduct. However, under the reaction conditions described for the first time here, acetaldehyde introduced additionally into the stream of reactants does not promote the reaction, but tends rather to have an inhibiting effect on the oxidation reaction.

In the process of the invention, the yields are over 7%, in particular over 8%, preferably >9%, at selectivities to propene oxide of >60%, in particular >61.5%. The propene conversions are >13%, in particular >14%, preferably >15%.

EXAMPLES

The invention is illustrated by the following examples, without any restriction being implied thereby.

The reactor comprises a vertical steel tube mounted near the bottom (length: 30 cm, of which 5.4 cm is reaction space length; internal diameter: 9.5 mm; reaction volume: 3.8 ml; steel no.: 1.4571) and is provided with a heatable outer jacket. The propene is metered in by means of a pump which conveys the liquefied alkene at a pressure of 100 bar into the reactor; the air is fed in via a mass flow regulator which makes it possible to operate the reactor with a constant volume flow. The pressure in the interior of the reactor is kept constant by means of a discharge valve at the reactor outlet. The composition of the product gas stream is determined by means of a gas chromatograph, which enables continuous analysis at chosen time intervals (taking into account the retention times of the products in the capillary column).

The following table shows a selection of results from the gas-phase oxidation reaction of propene with air:

Experiment 1 was carried out in a flow reactor made of standard steel with built-in standard NiCrNi thermocouples without other internals or lining with inert materials. Experiment 2 was carried out in the same reactor with gold-plated thermocouples. Experiment 3 was carried out in an otherwise identical reactor which was gold plated on the inside and provided with gold-plated thermocouples.

| No. | Temperature [° C.] | Proportion of propene [%] | Volume flow [ml/min] | Residence time [s] | Pressure [bar] | Propene conversion [%] | Yield [%] | PO selectivity [%] |
|---|---|---|---|---|---|---|---|---|
| 1 | 290 | 75 | 39.5 | 101.0 | 17.5 | 24.9* | 13.4 | <53.8 |
| 2 | 290 | 75 | 39.5 | 101.0 | 17.5 | 15.1 | 9.5 | 62.8 |
| 3 | 290 | 75 | 39.5 | 101.0 | 17.5 | 13.4 | 8.1 | 60.5 |

*Conversion includes oligomerization and polymerization products. The selectivity in Examples 2 and 3 is based only on oxidation products without taking into account oligomerization and polymerization products.

What is claimed is:

1. A process for preparing propene oxide, in which a mixture of propene and oxygen or an oxygen-containing gas is reacted in gas phase at a temperature in the range from 150 to 500° C., in the presence or absence of a catalyst, in a reactor, wherein all or part of the interior of the reactor is lined with gold.

2. The process as claimed in claim 1, wherein the inner walls of the reactor and/or internals for directing the gas stream are at least partially coated with gold or partially consist of gold.

3. The process as claimed in claim 1, wherein the residence time of the gas mixture in the reactor is from 0.1 to 15 minutes.

4. The process as claimed in claim 1, wherein the process is carried out at a reactor pressure in the range from 1 to 100 bar.

5. The process as claimed in claim 1, wherein the selectivity to propene oxide is >60%.

* * * * *